(12) United States Patent
Abernathie et al.

(10) Patent No.: US 7,909,843 B2
(45) Date of Patent: Mar. 22, 2011

(54) ELONGATEABLE SURGICAL PORT AND DILATOR

(75) Inventors: Dennis Lee Abernathie, Columbia, MO (US); Anthony J. Mulac, East Jordan, MI (US); Daniel K. Farley, Traverse City, MI (US)

(73) Assignee: Thompson Surgical Instruments, Inc., Traverse City, MI (US)

( * ) Notice: Subject to any disclaimer, the term of this patent is extended or adjusted under 35 U.S.C. 154(b) by 1040 days.

(21) Appl. No.: 10/880,824

(22) Filed: Jun. 30, 2004

(65) Prior Publication Data

US 2006/0004401 A1 Jan. 5, 2006

(51) Int. Cl.
*A61M 29/00* (2006.01)
*A61B 1/32* (2006.01)
*A61B 17/34* (2006.01)

(52) U.S. Cl. .......... 606/191; 606/198; 600/233

(58) Field of Classification Search .......... 600/219, 600/201, 208, 215, 227, 228, 231, 232, 233; 606/108, 191, 198, 201, 264; 604/104, 106
See application file for complete search history.

(56) References Cited

U.S. PATENT DOCUMENTS

| 569,839 A | 10/1896 | Roeloffs |
| 2,450,194 A * | 9/1948 | Glaser ............ 600/232 |
| 3,384,077 A | 5/1968 | Gauthier |
| 3,470,872 A | 10/1969 | Grieshaber |
| 3,788,318 A | 1/1974 | Kim et al. |
| 3,789,852 A | 2/1974 | Kim et al. |

(Continued)

FOREIGN PATENT DOCUMENTS

DE 4020956 A1 1/1991

(Continued)

OTHER PUBLICATIONS

U.S. Appl. No. 10/165,991, filed Jun. 10, 2002, Robert E. Simonson.

*Primary Examiner* — (Jackie) Tan-Uyen T Ho
*Assistant Examiner* — Jing Rui Ou
(74) *Attorney, Agent, or Firm* — McAndrews, Held & Malloy, Ltd.

(57) ABSTRACT

A surgical port and dilator are useful for creating access to surgical sites having tortuous geometries and/or requiring relatively long and narrow access to the surgical site. The surgical port or dilator can be provided with an oblique distal end to facilitate placement and the displace tissue near angled surfaces. The surgical port can be inserted into the operative site following dilation in the same fashion as a conventional port. Once inserted, however, the surgical port may then be elongated to provide relatively long and narrow, elliptically-shaped access to the surgical site. The elongation of the port allows the surgeon access to long and narrow surgical sites, such as the spine, without having to expand radially. This reduces trauma to the patient. A locking means is also provided to hold the surgical port in the open position until a release mechanism is activated.

11 Claims, 11 Drawing Sheets

U.S. PATENT DOCUMENTS

| | | | |
|---|---|---|---|
| 3,875,595 A | 4/1975 | Froning | |
| 4,232,660 A | 11/1980 | Coles | |
| 4,440,168 A | 4/1984 | Warren | |
| 4,449,532 A | 5/1984 | Storz | |
| 4,481,947 A | 11/1984 | Chester | |
| 4,545,374 A | 10/1985 | Jacobson | |
| 4,573,448 A | 3/1986 | Kambin | |
| 4,617,922 A | 10/1986 | Griggs | |
| 4,620,460 A | 11/1986 | Gonzales, Jr. | |
| 4,686,972 A | 8/1987 | Kurland | |
| 4,736,738 A | 4/1988 | Lipovsek | |
| 4,747,394 A | 5/1988 | Watanabe | |
| 4,747,395 A * | 5/1988 | Brief | 600/210 |
| 4,798,111 A | 1/1989 | Cheeseman | |
| 4,803,976 A | 2/1989 | Frigg | |
| 4,817,587 A | 4/1989 | Janese | |
| 4,862,891 A | 9/1989 | Smith | |
| 4,863,423 A | 9/1989 | Wallace | |
| 4,882,958 A | 11/1989 | McNeeley | |
| 4,921,479 A | 5/1990 | Grayzel | |
| 4,971,038 A | 11/1990 | Farley | |
| 5,035,232 A | 7/1991 | Lutze et al. | |
| 5,048,379 A | 9/1991 | Gramera | |
| 5,052,373 A | 10/1991 | Michelson | |
| 5,084,043 A | 1/1992 | Hertzmann | |
| 5,098,435 A | 3/1992 | Stednitz et al. | |
| 5,106,376 A | 4/1992 | Mononen et al. | |
| 5,125,396 A | 6/1992 | Ray | |
| 5,133,720 A | 7/1992 | Greenberg | |
| 5,135,525 A | 8/1992 | Biscoping | |
| 5,148,724 A | 9/1992 | Rexford | |
| 5,158,543 A | 10/1992 | Lazarus | |
| 5,171,279 A | 12/1992 | Mathews | |
| 5,195,541 A | 3/1993 | Obenchain | |
| 5,246,424 A | 9/1993 | Wilk | |
| 5,275,611 A | 1/1994 | Behl | |
| 5,279,567 A | 1/1994 | Ciaglia | |
| 5,292,309 A | 3/1994 | Van Tassel | |
| 5,303,694 A | 4/1994 | Mikhail | |
| 5,312,360 A | 5/1994 | Behl | |
| 5,356,413 A | 10/1994 | Martins | |
| 5,363,841 A | 11/1994 | Coker | |
| 5,431,639 A | 7/1995 | Shan | |
| 5,431,651 A | 7/1995 | Globe | |
| D361,381 S | 8/1995 | Koros | |
| 5,439,464 A | 8/1995 | Shapiro | |
| 5,472,426 A | 12/1995 | Bonati et al. | |
| 5,489,274 A | 2/1996 | Chu et al. | |
| 5,512,038 A | 4/1996 | O'Neal | |
| 5,569,248 A | 10/1996 | Mathews | |
| 5,601,550 A | 2/1997 | Esser | |
| 5,611,778 A | 3/1997 | Brinon | |
| 5,674,240 A * | 10/1997 | Bonutti et al. | 606/198 |
| 5,676,636 A * | 10/1997 | Chin | 600/209 |
| 5,687,739 A | 11/1997 | McPherson | |
| 5,716,415 A | 2/1998 | Steffee | |
| 5,728,097 A | 3/1998 | Mathews | |
| 5,743,853 A | 4/1998 | Lauderdale | |
| 5,746,720 A | 5/1998 | Stouder, Jr. | |
| 5,766,221 A | 6/1998 | Benderev | |
| 5,785,648 A * | 7/1998 | Min | 600/206 |
| 5,792,044 A | 8/1998 | Foley et al. | |
| 5,795,291 A * | 8/1998 | Koros et al. | 600/232 |
| D399,955 S | 10/1998 | Koros | |
| 5,816,257 A | 10/1998 | Chin | |
| RE36,020 E | 12/1998 | Moore | |
| 5,851,207 A | 12/1998 | Cesarone | |
| 5,882,344 A | 3/1999 | Stouder, Jr. | |
| 5,885,300 A | 3/1999 | Tokuhashi | |
| 5,891,147 A | 4/1999 | Moskovitz | |
| 5,895,352 A | 4/1999 | Kleiner | |
| 5,895,390 A | 4/1999 | Moran | |
| 5,897,593 A | 4/1999 | Kohrs | |
| 5,899,901 A | 5/1999 | Middleton | |
| 5,902,231 A | 5/1999 | Foley | |
| 5,913,818 A | 6/1999 | Co | |
| 5,928,139 A | 7/1999 | Koros | |
| 5,944,658 A | 8/1999 | Koros | |
| 5,954,635 A | 9/1999 | Foley | |
| 5,954,671 A | 9/1999 | O'Neill | |
| 5,967,970 A | 10/1999 | Cowan | |
| 5,971,920 A | 10/1999 | Nagel | |
| 5,976,146 A | 11/1999 | Ogawa | |
| 5,984,867 A * | 11/1999 | Deckman et al. | 600/232 |
| 5,996,447 A | 12/1999 | Bayouth | |
| 6,007,487 A | 12/1999 | Foley | |
| 6,010,520 A | 1/2000 | Pattison | |
| 6,033,406 A | 3/2000 | Mathews | |
| 6,042,540 A * | 3/2000 | Johnston et al. | 600/213 |
| 6,063,088 A | 5/2000 | Winslow | |
| 6,080,155 A | 6/2000 | Michelson | |
| 6,081,741 A | 6/2000 | Hollis | |
| 6,083,154 A * | 7/2000 | Liu et al. | 600/234 |
| 6,083,225 A | 7/2000 | Winslow | |
| 6,113,602 A | 9/2000 | Sand | |
| 6,120,434 A | 9/2000 | Kimura | |
| 6,120,506 A | 9/2000 | Kohrs | |
| D433,296 S | 11/2000 | Yamakawa | |
| 6,152,871 A | 11/2000 | Foley | |
| 6,156,006 A | 12/2000 | Brosens | |
| 6,159,179 A | 12/2000 | Simonson | |
| 6,162,170 A | 12/2000 | Foley | |
| 6,162,236 A | 12/2000 | Osada | |
| D436,513 S | 1/2001 | Yamakawa | |
| 6,176,823 B1 | 1/2001 | Foley | |
| D438,074 S | 2/2001 | Marr | |
| 6,197,002 B1 | 3/2001 | Peterson | |
| 6,206,822 B1 | 3/2001 | Foley | |
| 6,206,826 B1 | 3/2001 | Mathews | |
| 6,206,885 B1 | 3/2001 | Ghahremani | |
| 6,214,004 B1 | 4/2001 | Coker | |
| 6,217,509 B1 | 4/2001 | Foley | |
| 6,224,597 B1 | 5/2001 | Coker | |
| 6,224,608 B1 | 5/2001 | Ciccolella | |
| 6,245,072 B1 | 6/2001 | Zdeblick | |
| 6,258,097 B1 | 7/2001 | Cook | |
| 6,267,763 B1 | 7/2001 | Castro | |
| 6,270,498 B1 | 8/2001 | Michaelson | |
| 6,283,966 B1 | 9/2001 | Houfburg | |
| 6,287,313 B1 | 9/2001 | Sasso | |
| 6,296,609 B1 | 10/2001 | Brau | |
| 6,312,432 B1 | 11/2001 | Leppelmeier | |
| 6,342,057 B1 | 1/2002 | Brace | |
| 6,348,058 B1 | 2/2002 | Melkent | |
| 6,354,176 B1 | 3/2002 | Nordlin | |
| 6,371,959 B1 | 4/2002 | Trice | |
| 6,371,968 B1 | 4/2002 | Kogasaka et al. | |
| 6,418,821 B1 | 7/2002 | Yamakawa | |
| 6,428,472 B1 | 8/2002 | Haas | |
| 6,461,330 B1 | 10/2002 | Miyagi | |
| D466,766 S | 12/2002 | Marty | |
| 6,520,907 B1 | 2/2003 | Foley et al. | |
| 6,530,926 B1 | 3/2003 | Davison | |
| 6,540,756 B1 | 4/2003 | Vaughan | |
| 6,692,434 B2 | 2/2004 | Ritland | |
| 6,712,795 B1 * | 3/2004 | Cohen | 604/233 |
| 6,761,725 B1 * | 7/2004 | Grayzel et al. | 606/174 |
| 6,793,656 B1 | 9/2004 | Mathews | |
| 6,916,330 B2 | 7/2005 | Simonson | |
| 6,945,933 B2 * | 9/2005 | Branch et al. | 600/210 |
| 2001/0012942 A1 | 8/2001 | Estes | |
| 2001/0027320 A1 | 10/2001 | Sasso | |
| 2001/0029353 A1 | 10/2001 | Peterson | |
| 2001/0053922 A1 | 12/2001 | Zhu et al. | |
| 2002/0011135 A1 | 1/2002 | Hall | |
| 2002/0016592 A1 | 2/2002 | Branch | |
| 2002/0022764 A1 | 2/2002 | Smith | |
| 2002/0049368 A1 | 4/2002 | Ritland | |
| 2002/0058948 A1 | 5/2002 | Arlettaz | |
| 2002/0077632 A1 | 6/2002 | Tsou | |
| 2002/0082695 A1 | 6/2002 | Neumann | |
| 2002/0107574 A1 | 8/2002 | Boehm, Jr. et al. | |

| | | |
|---|---|---|
| 2002/0123668 A1 | 9/2002 | Ritland |
| 2002/0133128 A1 | 9/2002 | Heller |
| 2002/0143235 A1 | 10/2002 | Pagliuca |
| 2003/0083688 A1 | 5/2003 | Simonson |
| 2003/0083689 A1 | 5/2003 | Simonson |
| 2003/0187431 A1 | 10/2003 | Simonson |
| 2003/0220689 A1 | 11/2003 | Ritland |
| 2003/0236447 A1 | 12/2003 | Ritland |
| 2004/0106997 A1 | 6/2004 | Lieberson |

FOREIGN PATENT DOCUMENTS

| | | |
|---|---|---|
| DE | 20016971 U1 | 12/2000 |
| DE | 20015355 U1 | 2/2001 |
| WO | WO 00/18306 | 9/1999 |
| WO | WO 02/60330 | 1/2002 |
| WO | WO-2004/032807 A | 4/2004 |

* cited by examiner

ELONGATEABLE SURGICAL PORT AND DILATOR

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The disclosed inventions relate to surgical ports and associated dilators. In particular, the inventions relate to surgical ports and dilators useful for minimally invasive surgery.

In the past, surgery typically required large incisions to provide visual and instrument access to the surgical site. These large incisions resulted in significant blood loss, damage to muscle tissue, long healing times accompanied by prolonged pain, and significant scarring. Today, however, many surgeries are conducted using minimally invasive techniques. These techniques minimize patient trauma by creating a relatively small incision, followed by the introduction of dilators to increase the effective size of the incision. Following dilation, surgery is performed through a surgical port inserted into the dilated incision. Instead of cutting through the muscle surrounding the surgical site, dilation effectively splits the muscle. Splitting, rather than cutting the muscle causes less damage to the muscle and leads to faster recovery times and reduced patient discomfort.

Dilators develop a channel from the subcutaneous layer of a patient to the site of operation. A small incision, paralleling any underlying muscle, is made slightly longer than ½ the circumference of the largest dilator, or if used, port. A solid, pointed rod, variously described as a first dilator or guidewire, is then inserted into the incision to penetrate the underlying structures and reach the surgical site. It is best if the rod can be positioned against a bony surface as application of the dilators will attempt to push this rod forward. X-rays may be taken before and/or after insertion of the rod to confirm placement at the desired surgical site.

Increasingly larger diameter dilators can then be sequentially placed over each other to enlarge the channel. The larger diameter of the sequential dilators help to dilate the path of exposure while the series of tubes lessens the forces needed to create the path. The pointed tip of the dilators eases insertion and helps to widen the base of the channel when the dilator is orbited around a central axis formed through the center of the dilator along its length at the level of the skin.

In lieu of dilation, mechanical retractors can be used. Mechanical surgical retractors are hand-held or table-mounted metal retractor blades that are inserted into the incision, and thereafter retracted and held or locked in place to increase the effective opening of the incision. A drawback of using retractors is that, in comparison to dilators, a relatively large incision must be made to provide for placement of the retractor blades. Dilators and surgical ports, on the other hand, typically gain access to the surgical site by making a smaller incision, inserting a small probe into the incision, and then creating a progressively larger circular opening by repeatedly sliding larger dilators over the probe, thereby splitting the muscle. This splitting of the muscle is less traumatic and therefore offers a quicker post surgery recovery.

Conventional dilators and surgical ports, however, are not suitable for all surgical applications. For example, conventional dilators are unable to completely dilate muscle away from the lamina of the spine due to the tortuous geometry of the lamina. Thus, muscle located between the dilator and the lamina must typically be cut away to access the lamina when using conventional dilators.

Due to the geometry of the spine, many spinal surgical procedures require a long, narrow opening. Thus, another drawback of dilators is that a circular opening is not practical for most spinal surgeries because of the limited access it offers to the spine given the size of the dilated opening. The use of dilators and surgical ports are therefore generally limited to procedures involving very precise access to the spine, such as for single level discectomy.

Mechanical retractors, on the other hand, offer the promise of a long, narrow opening. As discussed above, however, mechanical retractors require a relatively large initial incision that involves cutting, rather than splitting of muscle.

Hence, there is a long-felt need for a device and method for enlarging minimally invasive incision by dilation, regardless of the orientation of the surgical access in relation to the surgical site. There is also a long-felt need for a device and method for enlarging minimally invasive incision by dilation that can displace muscle away from surgical sites possessing a tortuous geometry. Furthermore, there is also a long-felt need for a device and method for enlarging the dilated incision to create a long and narrow access to the surgical site by splitting, rather than cutting muscle surrounding the surgical site.

BRIEF SUMMARY OF THE INVENTION

A novel surgical port and dilator is provided for surgeons requiring a minimally invasive access to a surgical site. The present surgical port and dilator are particularly advantageous because the surgical port and/or the dilator can be configured with an oblique distal end. This oblique distal end is advantageous in surgeries where the surgical site is not level to the plane of the patient, e.g. spinal surgeries. Furthermore, various configurations of the oblique distal end of the surgical port and/or dilator facilitates the displacement of muscle from areas having tortuous geometries, such as the spinal lamina. In addition, the present surgical port can create a relatively long and narrow access to the surgical site by splitting the muscle surrounding the surgical site, rather than cutting it. The distal end of the surgical port can also be angled to accommodate the position of the surgical site in relation to the plane of the surgical access to the patient.

The present surgical dilators are inserted into a minimally invasive incision in the same fashion as a conventional dilator. Once inserted, however, the oblique distal end of the dilator can conform to a surgical site that is not aligned with the plane of the patient. Moreover, the dilator can be manipulated to maneuver along angled surfaces. In this case, the outer dilator can be replaced by one that is tapered on one or both sides. The tip of this taper can be placed against the highest portion of the base and then rotated, while keeping contact with bone, to the lowest point. In the spine, the tip begins at the base of the spinous process, rotates along the lamina, and comes to rest near the facet joint.

The outer dilator diameter is just under the inner diameter of the surgical port, and a surgical port with an oblique distal end can therefore be placed over the dilator, and the same motion repeated. This further clears muscle off of the bony base and helps move it to the periphery of the surgical port. With downward pressure on the surgical port, the dilators can be removed and the holding fixture can be applied.

The surgical port can also enlarge access to the surgical site, either in conjunction with dilators or by itself. The access created by the dilators is substantially circular, while the access created by the surgical port is relatively long and narrow. The elongation of the port allows the surgeon access surgical sites, such as the spine, where an expansion in diameter is not needed and may result in unnecessary trauma to the patient. A locking means is also provided to hold the surgical port in the open position until a release mechanism is activated.

BRIEF DESCRIPTION OF SEVERAL VIEWS OF THE DRAWINGS

A full and enabling disclosure of the present invention, including the best mode thereof, directed to one of ordinary skill in the art, is set forth in the specification, which makes reference to the appended figures, in which.

Repeat use of reference characters throughout the present specification and appended drawings is intended to represent same or analogous features or elements of the invention.

DETAILED DESCRIPTION OF THE INVENTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on or with another embodiment to yield a still further embodiment. Thus, it is intended that the present invention cover such modifications and variations. Other objects, features and aspects of the present invention are disclosed in or are apparent from the following detailed description. It is to be understood by one of ordinary skill in the art that the present discussion is a description of exemplary embodiments only, and is not intended as limiting the broader aspects of the present invention.

Figure 1:
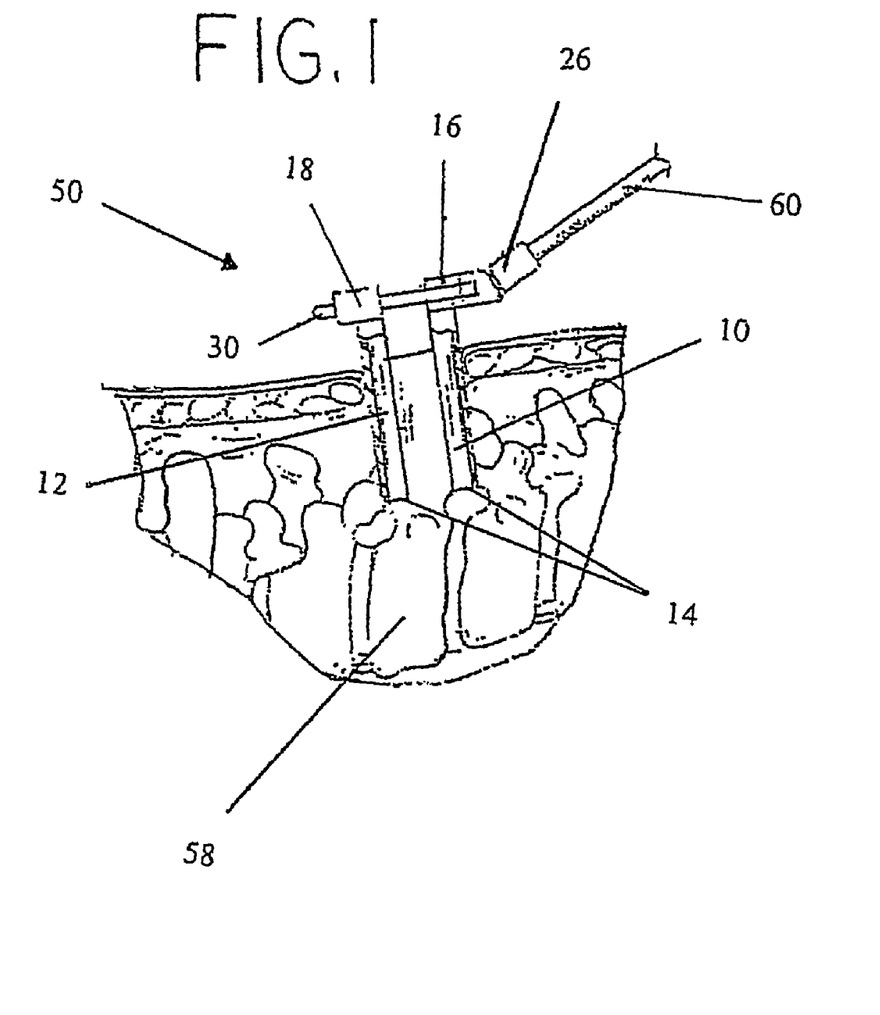
FIG. 1 is a side view of an exemplary extendable surgical port shown in an open position near a patient's spine.

To achieve increased access to the spinal area 58 for surgery, surgical port 50 can be elongated as shown in FIG. 1 to provide the desired relatively long and narrow access to spinal area 58. Prior to extension, however, closed surgical port 50 (see FIGS. 2 and 3) is first inserted into an incision over the surgical site, in this case spinal cord 58. Distal ends 14 of body segments 10 and 12 are positioned near surgical site 58. Once in place, immobilizer arm 60 can be attached to frame 54 using an adaptor 26. Immobilizer arm 60 is also attached to a stabilizing structure, such as the operating table (not shown), to steady surgical port 50.

Insertion of surgical port 50 in the closed position permits the surgeon to use a relatively small incision, and perhaps minimal dilation, thereby avoiding the large-scale cutting of muscle associated with increased access to spinal 58 provided by larger incisions. The desired increased access to spinal area 58 is instead created by elongating surgical port 50, thereby splitting and stretching the muscle, which minimizes cutting of the muscle.

Elongation of surgical port 50 is generally accomplished by sliding second body segment 12 away from first body segment 10 along frame arm 30. The resulting access to spinal area 58 is generally elliptical in shape due to the linear separation of generally semicircular body segments 10 and 12 (see FIG. 5). Surgery can then be performed through the long and narrow opening provided by elongated surgical port 50. In addition, a locking mechanism 62, depicted and discussed further in reference to FIGS. 2-8, can be employed to lock surgical port 50 in the desired elongated or closed position.

Following surgery on the surgical site 58, surgical port 50 can be closed, disconnected from immobilizer arm 60, and removed from the incision. The body will then close around and over the surgical site, and patient recovery times and pain levels during healing will be decreased.

Figure 2:
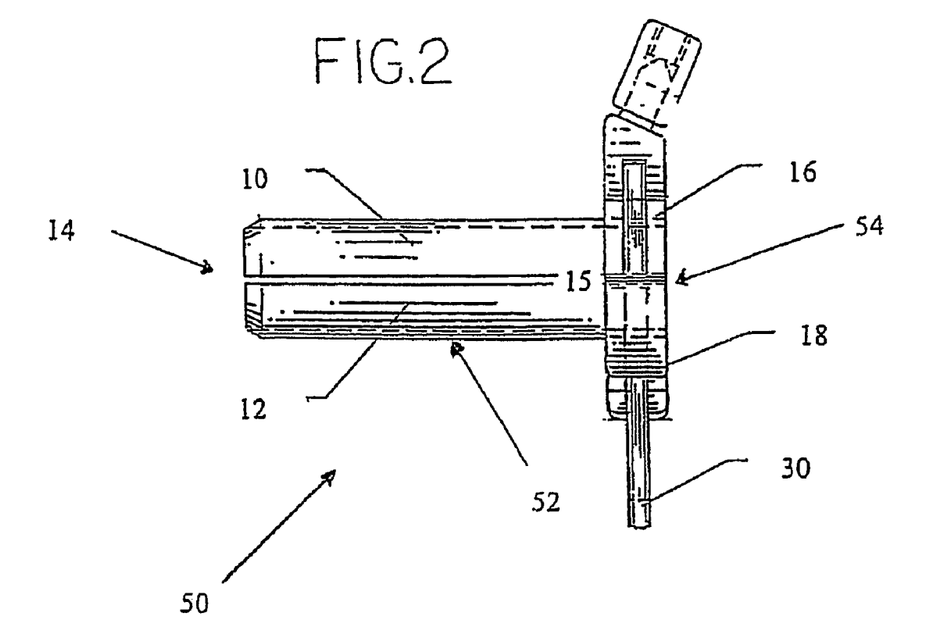
FIG. 2 is a side view of an exemplary extendable surgical port shown in the closed position.
Figure 3:
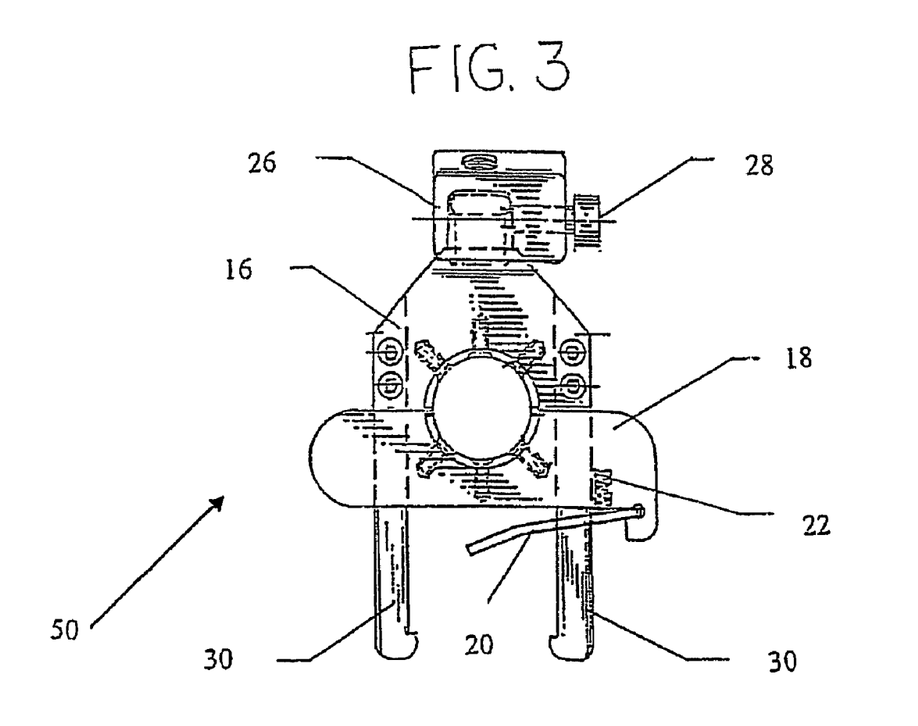
FIG. 3 is a top view of the closed surgical port of FIG. 2.

Referring now to FIGS. 2 and 3, this particular embodiment of surgical port 50 includes a frame 54 comprised of a first frame section 16 and a second frame section 18. Surgical port 50 also includes a body 52 comprising a first body segment 10 and a second body segment 12. Body segments 10 and 12 each have a distal end 14, and a proximal end 15. The proximal end 15 of first body segment 10 is attached to first frame section 16, and the proximal end 15 of second body segment 12 is attached to second frame section 18. Frame arms 30 are attached to first frame section 16, and extend through second frame section 18. An adaptor 26 is attached to first frame section 16 to facilitate the connection of the surgical port 50 to an operating table (not shown) or other stabilizing structure using one or more immobilizer arms 60 (see FIG. 1). An adaptor fastener 28 is used to attach adaptor 26 to first frame section 16. A locking mechanism, comprising a locking bar 20, in conjunction with second frame section 18, locking spring 22, and frame arms 30, serves to prevent the movement of first body segment 10 relative to second body segment 12, thereby holding surgical port 50 in an extended or closed position as required during the surgery. The locking mechanism is discussed further in reference to FIGS. 6 and 7.

Figure 4:
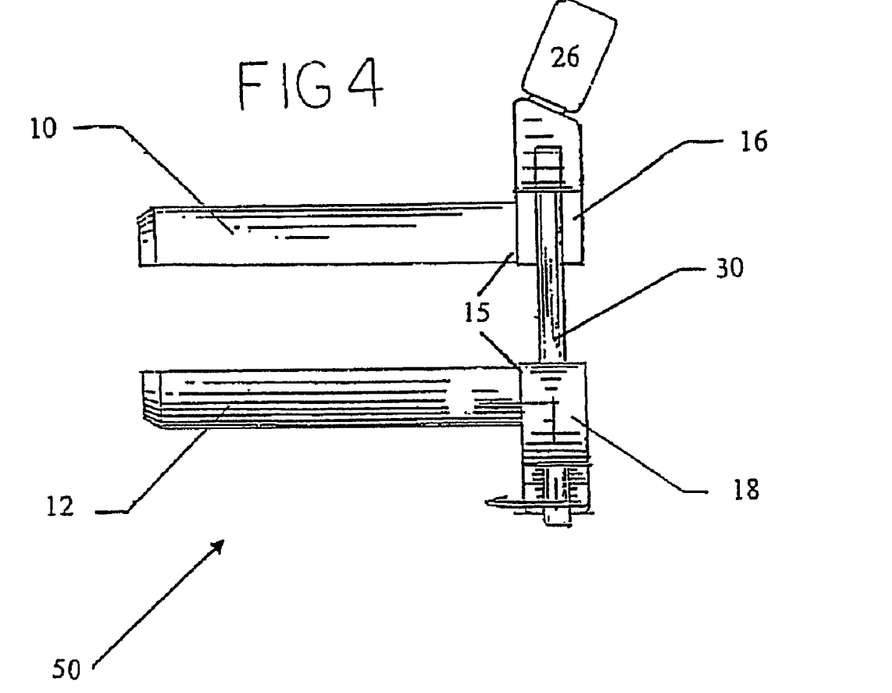
FIG. 4 is a side view of an exemplary extendable surgical port shown in an open position.
Figure 5:
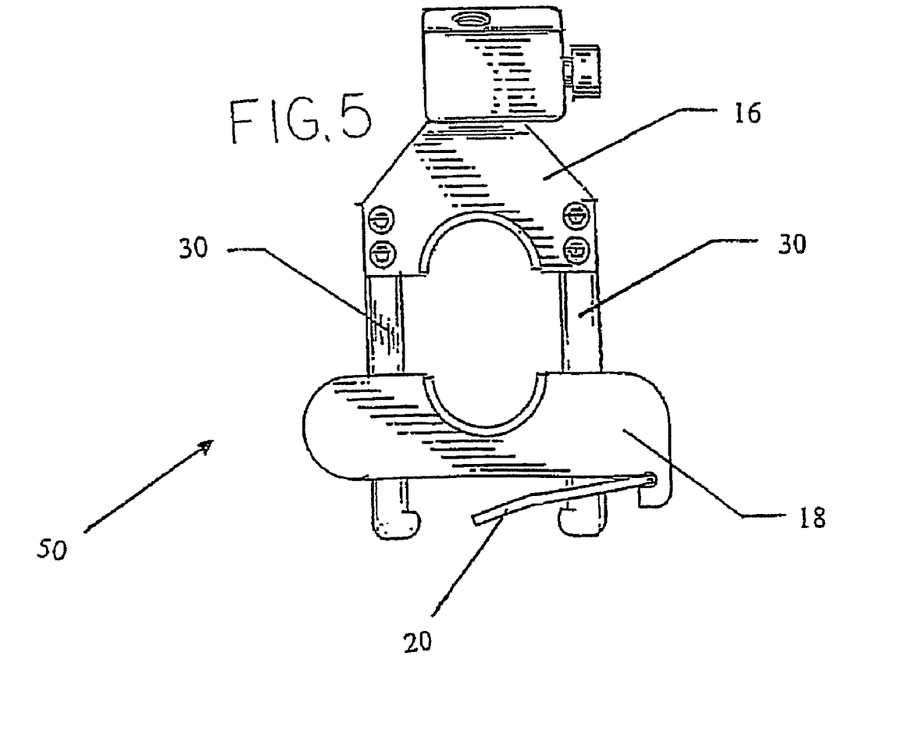
FIG. 5 is a top view of the open surgical port of FIG. 4.

FIGS. 4 and 5 depict surgical port 50 in an extended position. Relative to FIGS. 2 and 3, respectively, the second frame section 18 and attached second body segment 12 have moved away from the corresponding first frame section 16 and attached first body segment 10 along frame arms 30. Locking bar 20 is in the locked position. Notice the elongated, elliptical configuration of the resulting opening between first body segment 10 and second body segment 12 seen in FIG. 5.

It should be understood that while frame sections 16 and 18 and body segments 10 and 12 are depicted as separate pieces, an extendable surgical port having a unitary frame with frame sections and a unitary body with body segments is also contemplated. For example, frame sections 16 and 18 and body segments 10 and 12 could be joined by a flexible material (not shown) without departing from the scope of the extendable surgical port. Likewise, it should also be understood that although FIGS. 2 through 5 depict two frame arms 30, other configurations, such as a single frame arm (not shown) are also contemplated within the scope of the extendable surgical port. Other changes and variations may be made by those of ordinary skill in the art without departing from the spirit or the scope of the extendable surgical ports set forth in the claims.

Figure 6:
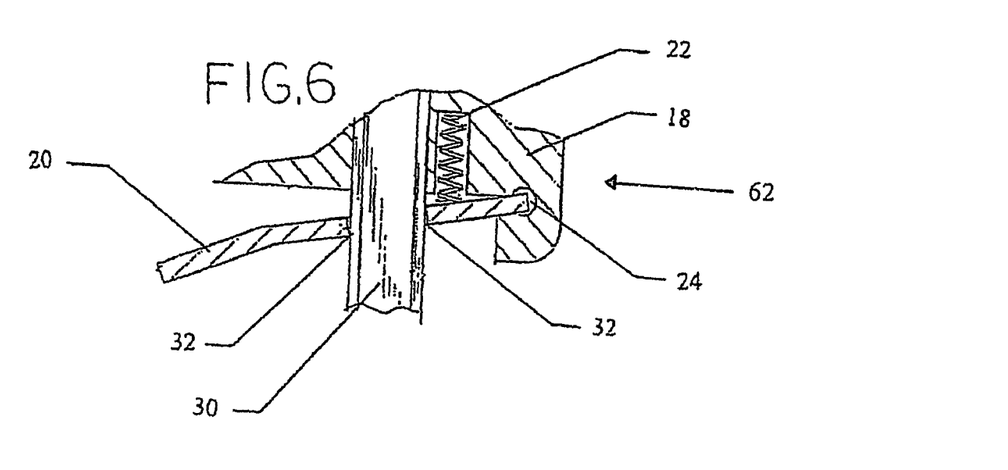
FIG. 6 is a cut-away side view of a locking mechanism, shown in the locked position for holding the surgical port in position.
Figure 7:
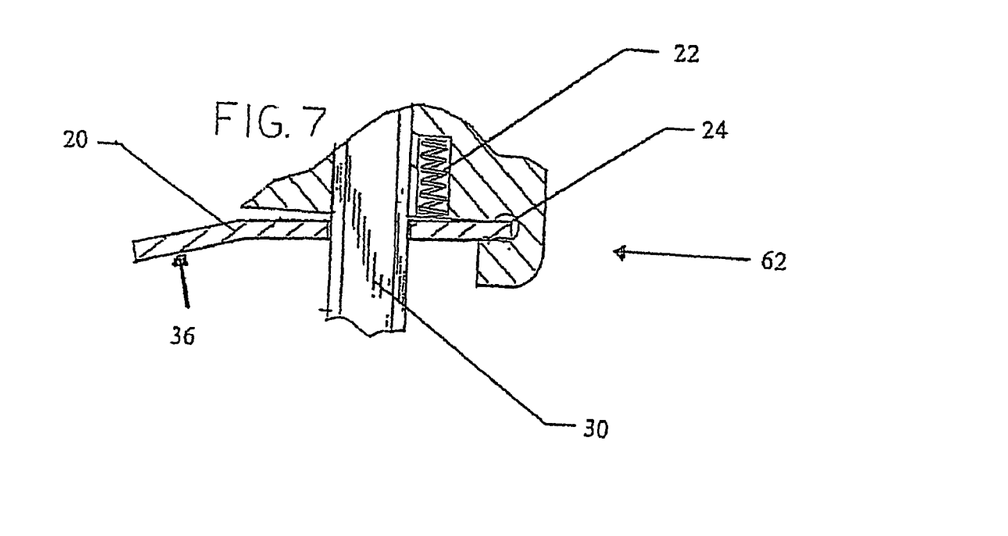
FIG. 7 is a cut-away side view of a locking mechanism, shown in the unlocked position for extending or closing the surgical port.

FIGS. 6 and 7 show the locking mechanism of surgical port 50 in the locked and unlocked positions, respectively. Referring to FIG. 6, the locking mechanism is in its normally locked position. Spring 22 has forced locking bar 20 to pivot in pivot point 24 in second frame section 18. Hole 34 in locking bar 20 (best seen in FIG. 8) is configured such that locking bar 20 engages frame arm 30 at contact points 32 somewhere along frame arm 30, depending on the position of second frame section 18, when spring 22 biases locking bar 20 away from second frame section 18.

FIG. 7 shows the locking mechanism in the unlocked position after force 36 is applied as shown. Force 36, easily applied by hand, overcomes the force applied by spring 22, pivoting locking bar 20 towards second frame section 18 and releasing the engagement of locking bar 20 with frame arm 30. Once second frame section 18 and attached second body segment 12 have reached a desired position relative to first frame section 16 and attached first body segment 10, the surgical port can be relocked by simply releasing force 36.

Figure 8:
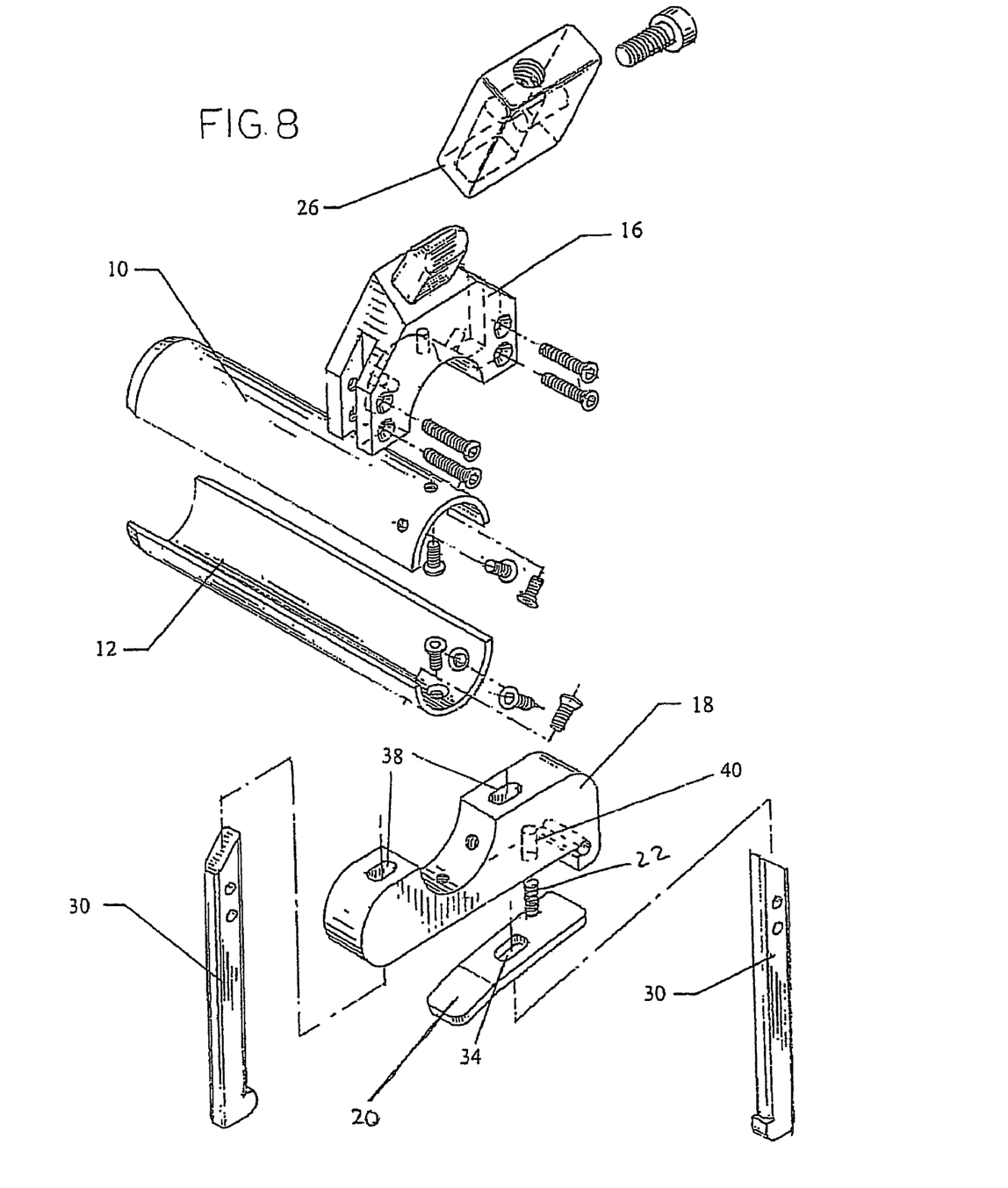
FIG. 8 is an exploded view of an exemplary extendable surgical port.

FIG. 8 depicts an exploded view of a presently preferred embodiment of surgical port 50. Note hole 34 in locking bar 20. The relationship of the assembled components is best visualized in this view. Frame arms 30 fit through holes 38 in second frame section 18. One frame arm 30 also fits through hole 34 in locking bar 20. Locking bar 20 pivots in pivot point 24 in second frame section 18, while spring 22 is partially recessed in recess 40 in second frame section 18. It is to be understood that although this presently preferred embodiment depicts screws as the attaching means for many parts of surgical port 50, such means of attachment are not limited to screws and instead encompass all methods of attachment known to those skilled in the art.

Figure 9:
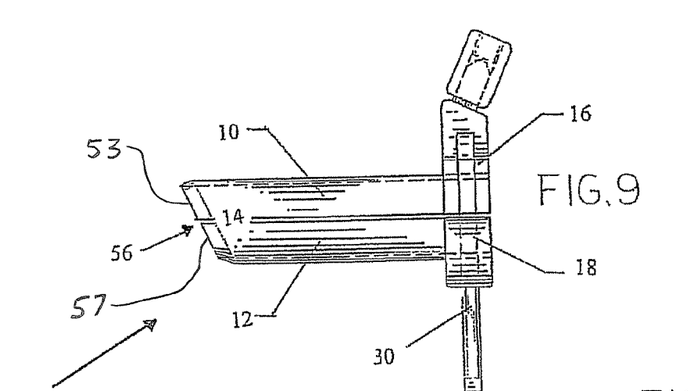
FIG. 9 is a side view of an exemplary extendable surgical port with an oblique distal end, shown in the closed position.

Since the anatomy of the spine is rarely level to the plane of the patient, it is often desirable to provide distal end 14 of surgical port body 52 with an oblique, or angled surface. FIG. 9 depicts another embodiment of surgical port 50 in the closed position. In this embodiment, the distal ends 14 of first body segment 10 and second body segment 12 are symmetrically oblique. In other words, the angled terminal surfaces 53, 57 of respective body segments 10 and 12 match up to form an angled terminal surface 56. Surgical port 50 embodying this feature can be selected to closely match the angle of the spine relative to the plane of the patient, resulting in surgical access close to the surgical site without impacting the spine.

Figure 10:
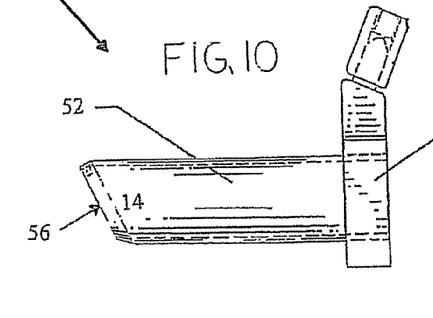
FIG. 10 is a side view of an exemplary non-extendable surgical port with an oblique distal end.
Figure 11:
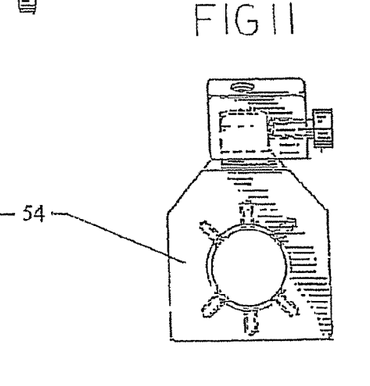
FIG. 11 is a top view of the non-extendable surgical port of FIG. 10.

FIGS. 10 and 11 depict yet another embodiment of surgical port 50. This embodiment is not extendable, and therefore body 52 does not include separate body segments 10 and 12. Similarly, frame 54 does not include frame sections 16 and 18. The distal end 14 of body 52, however, is still symmetrically oblique.

FIGS. 12 through 20 depict dilators 80 wherein opposing angles 84 of distal end 82 are asymmetrically oblique. The unique opposing, mismatched angled surfaces 84 of distal end 82 of dilator 80 allows for uneven splitting of muscle closest to the vertebral body or lamina. This configuration provides for customized access to the surgical site along the contours of an irregular surface, such as the spine. In FIGS. 12, 13, 16, and 19, the opposing angles 84 of distal end 82 and/or central opening 86 of dilator 80 are depicted using dotted lines. Top views of distal end 82 in FIGS. 14, 17, and 20 emphasize the difference between opposing angles depicted in FIGS. 13, 16, and 19 respectively.

Figure 12:
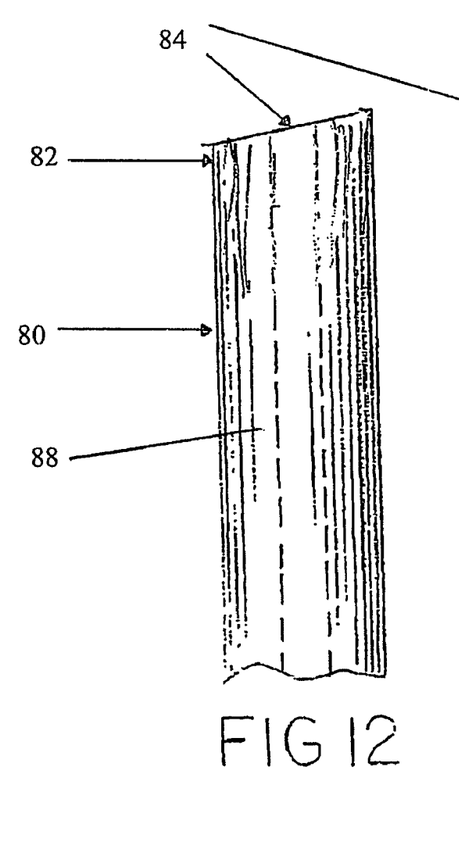
FIG. 12 is a first partial side view of the body of an exemplary dilator having an oblique distal end.
Figure 13:
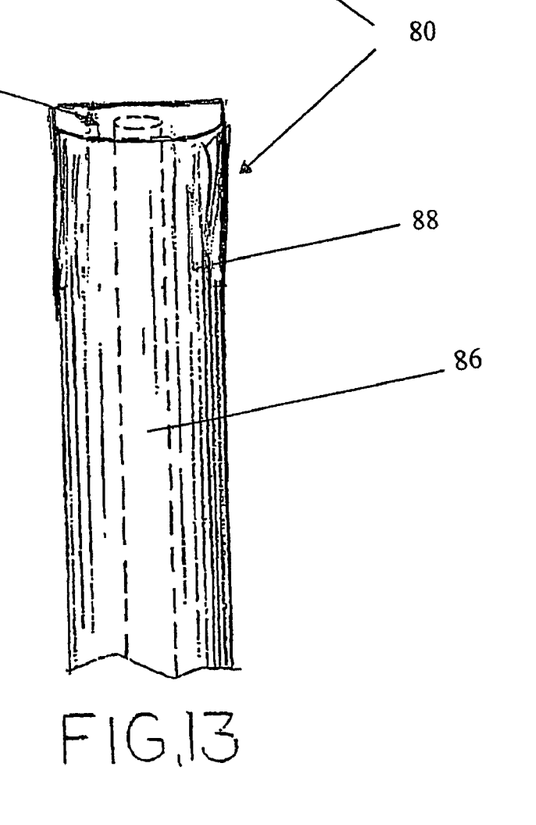
FIG. 13 is a second partial side view of the body of the exemplary dilator shown in FIG. 12 rotated ninety degrees from the position shown in FIG. 12.
Figure 14:
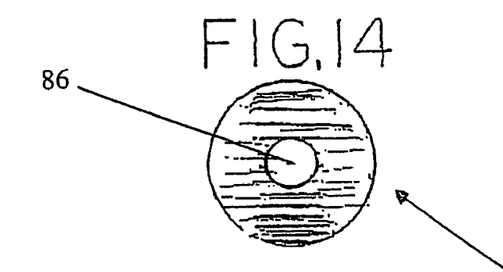
FIG. 14 is top view of the distal end of the body of the exemplary dilator shown in FIG. 13.

FIG. 12 depicts dilator 80 having a central opening 86 in a body 88 and a symmetrically oblique distal end 82. Angled surface 84 is merely representative of a symmetrically oblique configuration and should be considered only one embodiment of this aspect of the present dilator. Depending on the particular situation, a multitude of other angles could be used to provide angled surface 84. FIG. 13 represents dilator 80 of FIG. 12 rotated ninety degrees to further illustrate angled surface 84. FIG. 14 is a top view of dilator 80 of FIG. 13.

Figures 15, 16:
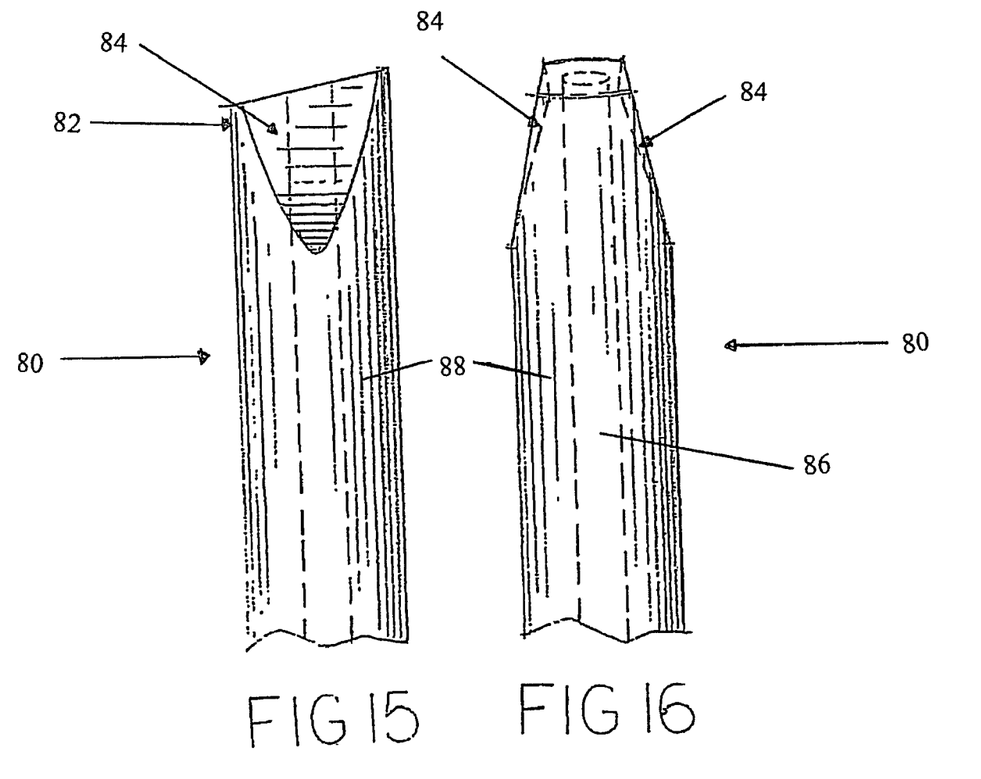
FIG. 15 is a first partial side view of the body of an exemplary dilator depicting a first configuration of an asymmetrical oblique distal end.
FIG. 16 is a second partial side view of the body of the exemplary dilator shown in FIG. 15 rotated ninety degrees from the position shown in FIG. 15.
Figure 17:
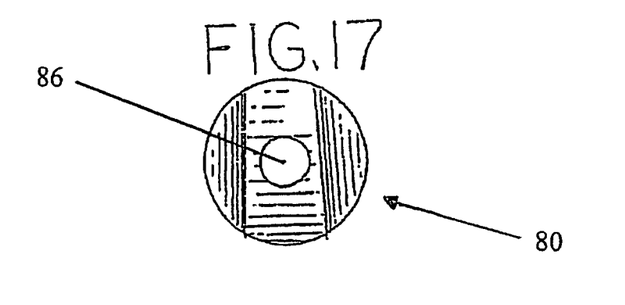
FIG. 17 is top view of the distal end of the body of the exemplary dilator shown in FIG. 16.

FIG. 15 depicts dilator 80 having a central opening 86 in a body 88 and an asymmetrically oblique distal end 82. Opposing angled surfaces 84 are merely representative of an asymmetrically oblique configuration and should be considered only one embodiment of this aspect of the present dilator 80. Depending on the particular situation, a multitude of other angles could be to provide angled surfaces 84, including, but not limited to the configurations shown in FIGS. 18-23. FIG. 16 represents dilator 80 of FIG. 15 rotated ninety degrees to further illustrate angled surfaces 84. FIG. 17 is a top view of dilator 80 of FIG. 16.

Figure 18:
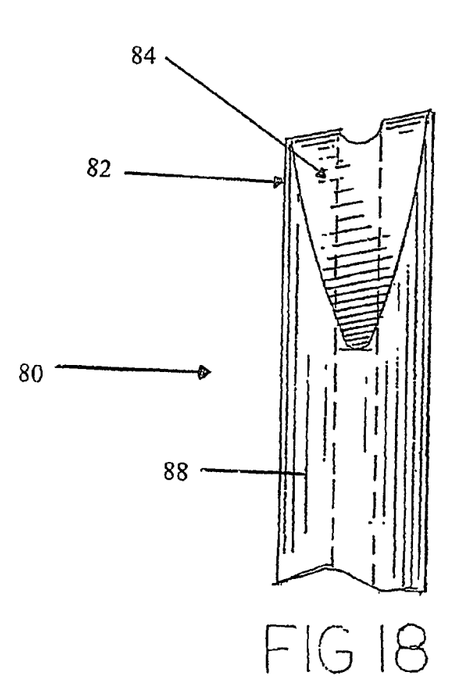
FIG. 18 is a first partial side view of the body of an exemplary dilator depicting a second configuration of an asymmetrical oblique distal end.
Figure 19:
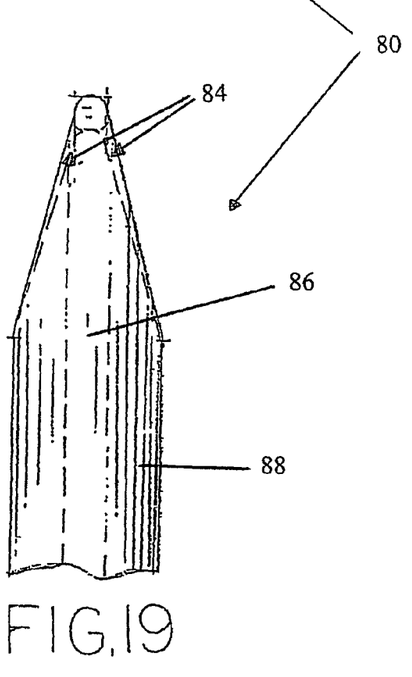
FIG. 19 is a second partial side view of the body of the exemplary dilator shown in FIG. 18 rotated ninety degrees from the position shown in FIG. 18.
Figure 20:
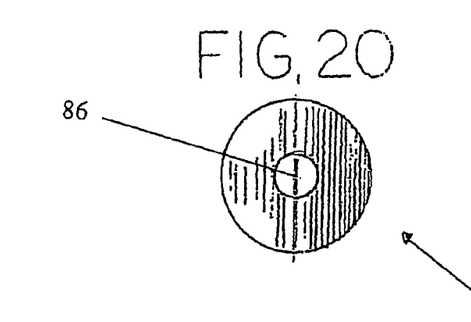
FIG. 20 is top view of the distal end of the body of the exemplary dilator shown in FIG. 19.

FIG. 18 depicts dilator 80 having a central opening 86 in a body 88 and an asymmetrically oblique distal end 82. Opposing angled surfaces 84 are merely representative of an asymmetrically oblique configuration and should be considered only one embodiment of this aspect of the present dilator. Depending on the particular situation, a multitude of other angles could be used to provide angled surfaces 84, including, but not limited to those configurations shown in FIGS. 15-17 and FIGS. 21-23. FIG. 19 represents dilator 80 of FIG. 15 rotated ninety degrees to further illustrate angled surfaces 84. FIG. 20 is a top view of dilator 80 of FIG. 16.

Figure 21:
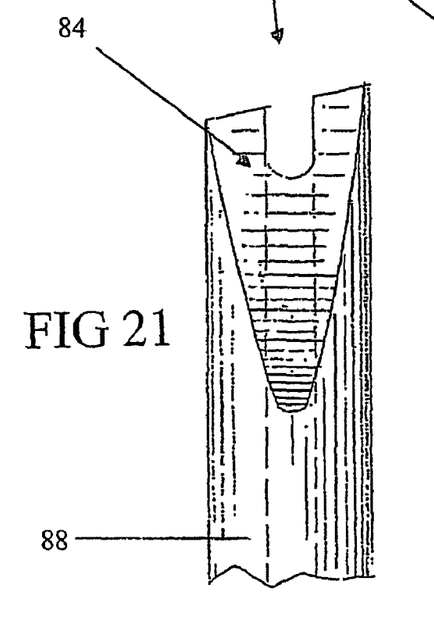
FIG. 21 is a first partial side view of the body of an exemplary dilator depicting a third configuration of an asymmetrical oblique distal end.
Figure 22:
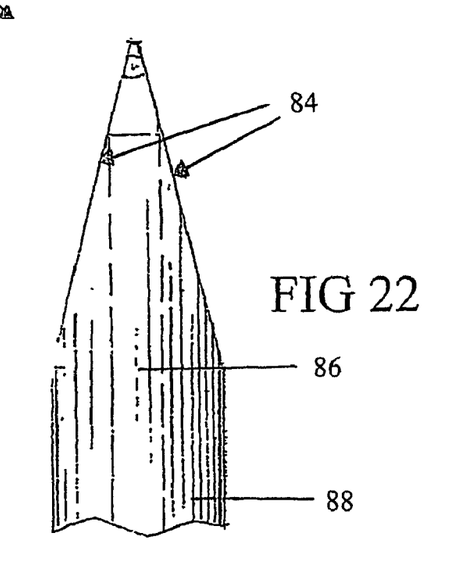
FIG. 22 is a second partial side view of the body of the exemplary dilator shown in FIG. 21 rotated ninety degrees from the position shown in FIG. 21.
Figure 23:
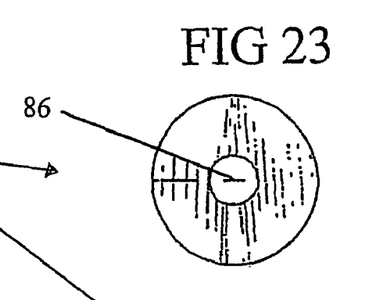
FIG. 23 is top view of the distal end of the body of the exemplary dilator shown in FIG. 22.

FIG. 21 depicts dilator 80 having a central opening 86 in a body 88 and an asymmetrically oblique distal end 82. Opposing angled surfaces 84 are merely representative of an asymmetrically oblique configuration and should be considered only one embodiment of this aspect of the present dilator. Depending on the particular situation, a multitude of other angles could be used to provide angled surfaces 84, including, but not limited to the configurations shown in FIGS. 15-20. FIG. 22 represents dilator 80 of FIG. 15 rotated ninety degrees to further illustrate angled surfaces 84. FIG. 23 is a top view of dilator 80 of FIG. 16.

Figure 24:
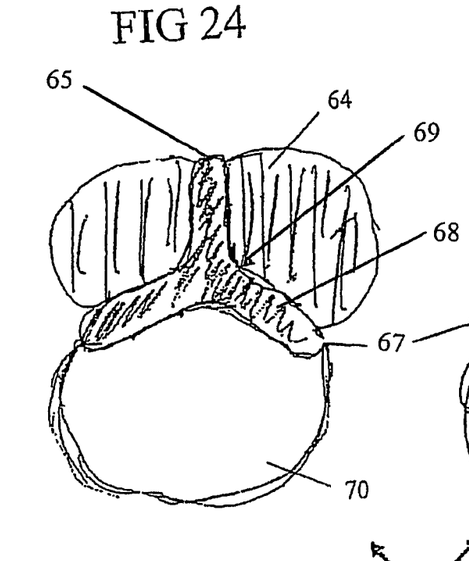
FIG. 24 depicts a cross section of a patient's spine.

FIGS. 24 through 27 depict dilator 80 in use near the spine 66. As shown in FIG. 24, the spine 66 includes muscles 64, lamina 68 (bone covering the spinal cord), and discs 70. Notice that lamina 68 creates obtuse angle 72 between the tip of the spinous process 65 and the facet joint 67. The area around obtuse angle 72 is surrounded by muscles 64. Conventional dilators 90 (see FIG. 25), are unable to remove sufficient muscle 64 from lamina 68, and therefore it is frequently necessary to cut portions of muscle 64 to provide surgical access to lamina 68.

Figure 25:
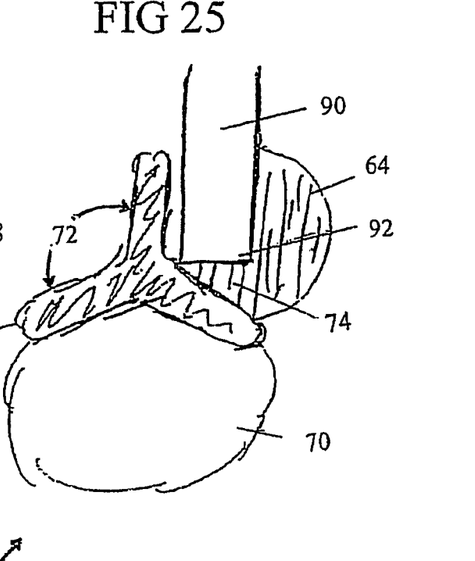
FIG. 25 depicts a cross section of conventional dilator inserted near a patient's spine.

To illustrate this problem, FIG. 25 represents a conventional dilator 90 inserted along lamina 68. The distal end 92 of conventional dilator 90 lacks the oblique configuration of the distal end 14 of present dilator 80. If conventional dilator 90 is manipulated near lamina 68, muscle 64 below distal end 92 of conventional dilator 90 in region 74 would continue to obstruct access to lamina 68 below the base of the spinous process 69. Thus, muscle 64 in region 74 would have to be cut away from lamina 68.

Figure 26:
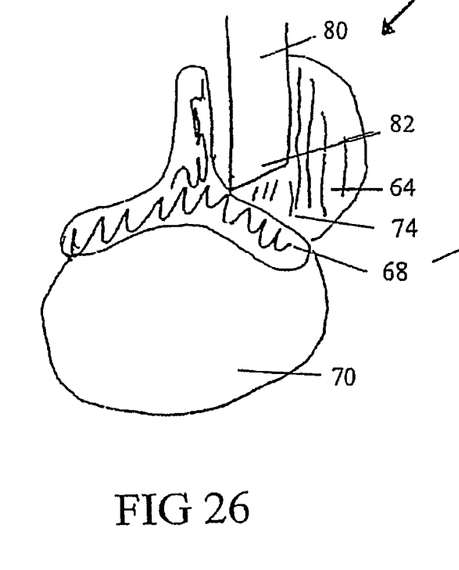
FIG. 26 depicts a cross section of a dilator having an oblique distal end following initial insertion near a patient's spine.
Figure 27:
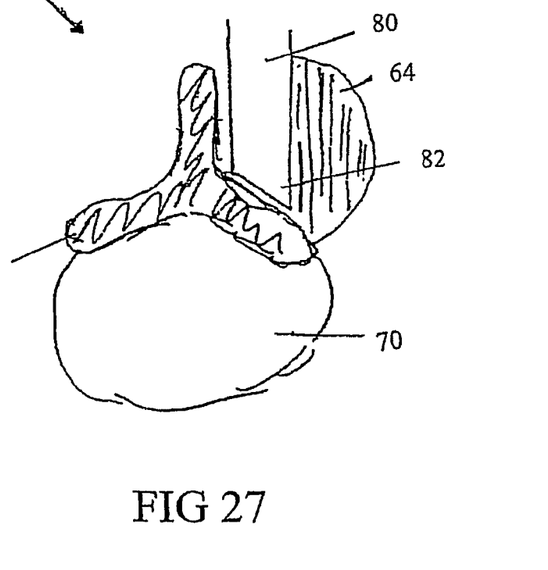
FIG. 27 depicts the dilator of FIG. 26 following manipulation of the dilator to displace muscle away from the spine.

In FIG. 26, however, present dilator 80 is provided with an oblique distal end 82 which is inserted until adjacent to lamina 68. Angled surface 84 of dilator 80 can then be maneuvered along lamina 68 by rotating and further inserting dilator 80 until muscle 64 in region 74 is maneuvered away from lamina 68 as seen in FIG. 27. Thus, access to the surgical site can be created without excessive cutting of muscle 64 in region 74.

Following dilation, an oblique surgical port 55 (depicted in FIGS. 9-11) may be inserted over present dilator 80. Angled terminal surface 56 of oblique surgical port 55 can be maneuvered along lamina 68 by rotating and further inserting oblique surgical port 55 until muscle 64 in region 74 is maneuvered away from lamina 68 in the same manner previously discussed with respect to dilation and FIG. 27. Alternatively, oblique surgical port 55 may be used after conventional dilation to maneuver muscle 64 in region 74 away from lamina 68.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present surgical port, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. An extendable surgical port comprising:
   a first body segment having a proximal end and a distal end opposite the proximal end;
   a second body segment having a proximal end and a distal end opposite the proximal end;
   a first frame section attached to the proximal end of the first body segment;
   a second frame section attached to the proximal end of the second body segment;
   a first frame arm attached to the first frame section and the second frame section such that the second frame section is slidable along the first frame arm relative to the first frame section between a closed position and an extended position;
   a locking bar engageable with the second frame section and the first frame arm to secure the second frame section relative the first frame arm by directly contacting the locking bar with at least one contact point on the first frame arm, wherein the contact point is not a notched surface, wherein the locking bar includes a hole configured to receive the first frame arm, and wherein the locking bar is configured to extend from a pivot point on the second frame section; and
   a spring disposed between the locking bar and the second frame section, the spring configured to bias the locking bar about the pivot point, wherein the spring is recessed into the second frame section, wherein the locking bar is configured such that pivoting the locking bar about the pivot point toward the second frame section compresses the spring toward the second frame section and releases contact between the locking bar and the first frame arm, thereby unsecuring the second frame section such that the second frame section is slidable along the first frame arm.

2. The extendable surgical port of claim 1, further comprising an adapter attached to the first frame section, the adapter engageable with an immobilizer arm.

3. The extendable surgical port of claim 1, further comprising a second frame arm attached to the first frame section and the second frame section such that the second frame section is slidable along both the first and second frame arms.

4. The extendable surgical port of claim 1, wherein the distal end of the first body segment and the distal end of the second body segment are oblique such that a terminal surface of each body segment is angled.

5. The extendable surgical port of claim 4, wherein the oblique distal end of the first body segment and the oblique distal end of the second body segment are symmetrical such that the angled terminal surfaces match up to provide an angled terminal surface when in the closed position.

6. The extendable surgical port of claim 1, wherein an opening between the first body segment and the second body segment is generally circular in cross section when the surgical port is in the closed position, and wherein the opening is generally elliptical in cross section when the surgical port is in the extended position.

7. The extendable surgical port of claim 1, wherein the locking bar is configured such that the locking bar contacts the first frame arm, thereby securing the second frame section such that the second frame section cannot slide along the first frame arm, when a force that would pivot the locking bar about the pivot point toward the second frame section is not being applied.

8. The extendable surgical port of claim 1, wherein the spring is configured to bias the locking bar about the pivot point away from the second frame section.

9. The extendable surgical port of claim 1, wherein the spring is a coil spring.

10. The extendable surgical port of claim 1, wherein the hole is an elongated hole.

11. The extendable surgical port of claim 1, wherein the locking bar comprises a lever configured to extend from the pivot point on the second frame section.

* * * * *